(12) United States Patent
Pedersen et al.

(10) Patent No.: US 12,428,657 B2
(45) Date of Patent: Sep. 30, 2025

(54) HMO PRODUCTION

(71) Applicant: GLYCOM A/S, Hørsholm (DK)

(72) Inventors: Margit Pedersen, Roskilde (DK);
Katrine Bych Kampmann, Valby (DK)

(73) Assignee: GLYCOM A/S, Hørsholm (DK)

( * ) Notice: Subject to any disclaimer, the term of this patent is extended or adjusted under 35 U.S.C. 154(b) by 473 days.

(21) Appl. No.: 17/759,273

(22) PCT Filed: Jan. 22, 2021

(86) PCT No.: PCT/EP2021/051472
§ 371 (c)(1),
(2) Date: Jul. 21, 2022

(87) PCT Pub. No.: WO2021/148614
PCT Pub. Date: Jul. 29, 2021

(65) Prior Publication Data
US 2023/0227876 A1 Jul. 20, 2023

(30) Foreign Application Priority Data
Jan. 23, 2020 (DK) .............................. PA202000086

(51) Int. Cl.
| C12P 19/00 | (2006.01) |
| C07K 14/195 | (2006.01) |
| C07K 14/24 | (2006.01) |
| C12P 19/04 | (2006.01) |

(52) U.S. Cl.
CPC ............ *C12P 19/00* (2013.01); *C07K 14/195* (2013.01); *C07K 14/24* (2013.01); *C12P 19/04* (2013.01)

(58) Field of Classification Search
CPC .......... C12P 19/00; C12P 19/04; C07K 14/24; C07K 14/195; Y02A 50/30
See application file for complete search history.

(56) References Cited

U.S. PATENT DOCUMENTS

| 8,652,808 | B2 * | 2/2014 | Jennewein ............. C12N 15/70 435/72 |
| 2019/0119314 | A1 | 4/2019 | Chassagne et al. |
| 2019/0323052 | A1 * | 10/2019 | Hollands .............. C12N 9/0006 |
| 2019/0323053 | A1 | 10/2019 | Laffend et al. |

FOREIGN PATENT DOCUMENTS

| EP | 2927316 A1 * | 10/2015 | ............. C12N 15/70 |
| EP | 3141610 | 3/2017 | |
| EP | 3315610 | 5/2018 | |
| EP | 3569713 | 11/2019 | |
| WO | WO 2010142305 | 12/2010 | |
| WO | WO 2012112777 | 8/2012 | |
| WO | WO 2015150328 | 10/2015 | |
| WO | WO 2015188834 | 12/2015 | |
| WO | WO 2016040531 | 3/2016 | |
| WO | WO 2016095924 | 6/2016 | |
| WO | WO 2017042382 | 3/2017 | |
| WO | WO 2017152918 | 9/2017 | |
| WO | WO 2017182965 | 10/2017 | |
| WO | WO 2018077892 | 5/2018 | |
| WO | WO 2019123324 | 6/2019 | |

OTHER PUBLICATIONS

Kumar S, Floyd JT, He G, Varela MF. Bacterial antimicrobial efflux pumps of the MFS and MATE transporter families: a review. Recent Res Dev Antimicrob Agents Chemother. 2013;7:1-21. (Year: 2013).*
Browning DF, Godfrey RE, Richards KL, Robinson C, Busby SJ. Exploitation of the *Escherichia coli* lac operon promoter for controlled recombinant protein production. Biochemical Society Transactions. Apr. 30, 2019;47(2):755-63. (Year: 2019).*
Reddy VS, Shlykov MA, Castillo R, Sun EI, Saier Jr MH. The major facilitator superfamily (MFS) revisited. The FEBS journal. Jun. 2012;279(11):2022-35. (Year: 2012).*
Weissenborn DL, Wittekindt N, Larson TJ. Structure and regulation of the glpFK operon encoding glycerol diffusion facilitator and glycerol kinase of *Escherichia coli* K-12. Journal of Biological Chemistry. Mar. 25, 1992;267(9):6122-31. (Year: 1992).*
Altschul et al. Nucl. Acids Res. 25, 3389 (1997).
Ausubel et al. (eds.), Current Protocols in Molecular Biology (1995) (John Wiley & Sons).
Ausubel et al., Current protocols in molecular biology, John Wiley and Sons (2010).
Chen, Adv. Carbohydr. Chem. Biochem. 72, 113 (2015).
Chichlowski M. et al (2012) J. Pediatr. Gastroenterol. Nutr. 55(3):321-327.
Elison E. et al., (2016) Brit J. Nutr, 116: 1356-1368.
Herring, C.D., Glasner, J.D. and Blattner, F.R. (2003). Gene (311). 153-163.
Hollands et al., (2019) Methabolic Eng 52:232-242.
Kunz C. et al., (2014) Food Oligosaccharides: Production, Analysis and Bioactivity, 1st Edition, p. 5-20, Eds. Moreno J. and Luz Sanz M., John Wiley & Sons, Ltd.
Murphy, J Bacteriol.j (1998); 180(8): 2063-7.
Muyrers et al., EMBO Rep. (2000) 1(3): 239-243.
Reddy V.S. et al., (2012), FEBS J. 279(11): 2022-2035.
Urashima et al.: Milk Oligosaccharides. Nova Science Publisher (2011).
Vetcher et al., App/ Environ Microbiol. (2005); 71(4):1829-35.
Waddell C.S. and Craig N.L., Genes Dev. Feb. 1988;2(2):137-49.

(Continued)

*Primary Examiner* — Sharmila G Landau
*Assistant Examiner* — Emily F Eix
(74) *Attorney, Agent, or Firm* — Neal, Gerber & Eisenberg LLP

(57) ABSTRACT

The present invention relates to the field of recombinant production of biological molecules in host cells. More particularly it relates to a method for recombinant production of human milk oligosaccharides (HMO) using a genetically modified cell expressing a protein of the major facilitator superfamily (MFS).

15 Claims, 3 Drawing Sheets
Specification includes a Sequence Listing.

(56) References Cited

OTHER PUBLICATIONS

Wenzel et al., Chem Biol. (2005), 12(3):349-56.
Wilson K. and Walker J., Principles and Techniques of Biochemistry and Molecular Biology (2010), Cambridge University Press.
Yu et al.,(2018) Microb Cell Fact 17:101.
Zhang et al., Nature Genetics (1998) 20: 123-128.
Neubauer, P., et al., "Efficient use of lactose for the lac promoter-controlled overexpression of the main antigenic protein of the foot and mouth disease virus in *Escherichia coli* under fed-batch fermentation conditions," FEMS Microbiology Reviews, 1994, vol. 14, pp. 99-102.
Pao, S.S., et al., "Major Facilitator Superfamily," Microbiology and Molecular Biology Reviews, 1998, vol. 62(1), pp. 1-34.
"MFS transporter [Serratia marcescens]", Genbank Accession: WP_060448169, Jun. 6, 2016.

* cited by examiner

SEQ ID NO: 1
MQRLSRLSLRINPIFAAFLLIAFLSGIAGALLTPTLSLFLTTEVKVRPLWVGLFYTANA
VAGIVVSFLLAKRSDTRGDRRRLILLCCLMAVGNCLLFAFNRDYLTLITAGVLMSAVA
NTAMPQIFALAREYADSEAREVVMFSSVMRAQLSLAWVIGPPLSFALALNYGFTVM
FLIAAVTFAVCVLLVGFMLPSVPRAAENEGLQGGVSAPIAPASAWRNRDVRLLFIAS
MLMWTCNTLYIIDMPLYITADLGLPEGLAGVLMGTAAGLEIPAMLLAGYYVKRFGKR
NMMLLAVVAGVLFYLGLTVLESKPALIALQLLNAVFIGIVAGIGMLYFQDLMPGRPGA
ATTLFTNSISTGVILAGVLQGALVENLGHGSVYWMAALLALAALGMSAKVREV

FIG. 3

HMO PRODUCTION

CROSS-REFERENCE TO RELATED APPLICATION

This application is a national stage entry pursuant to 35 U.S.C. § 371 of International Application No. PCT/EP2021/051472, filed on Jan. 22, 2021, which claims priority to Denmark Patent Application No. PA 2020 00086 filed Jan. 23, 2020, the contents of all of which are fully incorporated herein by reference.

TECHNICAL FIELD

The present invention relates to the field of recombinant production of biological molecules in host cells. More particularly it relates to a method for recombinant production of human milk oligosaccharides (HMO) using genetically modified cell expressing a protein of the major facilitator superfamily (MFS).

BACKGROUND OF THE INVENTION

Human milk oligosaccharides (HMOs) constitute the third largest solid component in human milk and are highly resistant to enzymatic hydrolysis. As a consequence, a substantial fraction of HMOs remains largely undigested and unabsorbed, which enables their passage through to the colon. In the colon, HMOs may serve as substrates to shape the gut ecosystem by selectively stimulating the growth of specific saccharolytic bacteria. This selectivity is viewed as beneficial for both infants and adults since strains of *Bifidobacterium* species are believed to have a positive effect on gut health (Chichlowski M. et al., (2012) J. Pediatr. Gastroenterol. Nutr. 5:251-258; Elison E. et al., (2016) Brit J. Nutr, 116: 1356-1368).

Besides their prebiotic properties, HMOs have been linked to additional positive effects, which expands their field of application (Kunz C. et al., (2014) Food Oligosaccharides: Production, Analysis and Bioactivity, 1st Edition, p 5-20, Eds. Moreno J. and Luz Sanz M., John Wiley & Sons, Ltd).

The obvious health benefits of HMOs have enabled their approval for use in foods, such as infant formulas and foods, and for consumer health products. Biotechnological production of HMOs is a valuable cost-efficient and large-scale way of HMO manufacturing. It relies on genetically engineered bacteria constructed so as to express the glycosyltransferases needed for synthesis of the desired oligosaccharides and takes advantage of the bacteria's innate pool of nucleotide sugars as HMO precursors. Recent developments in biotechnological production of HMOs have made it possible to overcome certain inherent limitations of bacterial expression systems. For example, HMO-producing bacterial cells may be genetically modified to increase the limited intracellular pool of nucleotide sugars in the bacteria (WO2012112777), to improve activity of enzymes involved in the HMO production (WO2016040531), or to facilitate the secretion of synthesized HMOs into the extracellular media (WO2010142305, WO2017042382). Further, expression of genes of interest in recombinant cells may be regulated by using particular promoters or other gene expression regulators, like e.g what has recently been described in WO2019123324.

The approach described in WO2010142305 and WO2017042382 has an advantage in that it allows to reduce the metabolic burden inflicted on the producing cell by high levels of recombinant gene expression, e.g. using methods of WO2012112777, WO2016040531 or WO2019123324. This approach attracts growing attention in recombinant HMO-producing cells engineering, e.g. recently there have been described several new sugar transporter genes encoding proteins and fermentation procedures that can facilitate efflux of a recombinantly produced 2'-fucosyllactose (2'-FL), the most abundant HMO of human milk (WO2018077892, US201900323053, US201900323052). However, at present, there is no algorithm that is able to pinpoint the right transporter protein capable of efflux of different recombinantly produced HMO structures among numerous bacterial proteins with predicted transporter function in multiple protein databases, e.g. UniProt, since the structures/factors defining substrate specificity of sugar transporters are still not well-studied and remain to be highly unpredictable.

SUMMARY OF THE INVENTION

Identification of new efficient sugar efflux transporter proteins having specificity for different recombinantly produced HMOs and development of recombinant cells expressing said protein are advantageous for high scale industrial HMO manufacturing.

This invention provides recombinant cells capable of producing a human milk oligosaccharide (HMO), wherein the cells are expressing a heterologous gene encoding a putative MFS (major facilitator superfamily) transporter protein, originating from the bacterium *Serratia marcescens*. More specifically, the invention relates to a genetically modified cell optimized for the production of an oligosaccharide, in particular an HMO, comprising a recombinant nucleic acid encoding a protein having at least 80% sequence similarity to the amino acid sequence of SEQ ID NO: 1 (FIG. 3). The amino acid sequence identified herein as SEQ ID NO: 1 is the amino acid sequence that is 100% identical to the amino acid sequence having the GenBank accession ID WP_060448169.1. The MFS transporter protein having the amino acid sequence of SEQ ID NO: 1 is identified herein as "Marc protein" or "Marc transporter" or "marc", interchangeably; a nucleic acid sequence encoding marc protein is identified herein as "Marc coding nucleic acid/DNA" or "marc gene" or "marc".

The present invention shows that use of HMO producing recombinant cells that express Marc protein results in very distinct improvements of the HMO manufacturing process related both to fermentation and purification of the HMOs. The disclosed herein recombinant cells and methods for HMO production provide both higher yields of total produced HMOs, lower by-product formation or by-product-to-product ratio, lower biomass formation per fermentation and facilitated recovery of the HMOs during downstream processing of the fermentation broth.

Surprisingly, expression of a DNA sequence encoding Marc in different HMO producing cells is found to be associated with accumulation of some particular HMOs in the extracellular media and other HMOs inside of the producing cells, and in an increase in total production of the HMOs. Surprisingly, an increase in the efflux of the produced HMOs is found to be characteristic for HMOs that consist of either tri or tetra units of monosaccharides, i.e. HMOs that are trisaccharides and tetrasaccharides, e. g, 2'-fucosyllactose (2'-FL), 3-fucosyllactose (3'-FL), 3-sialyllactose (3'-SL), 6'-sialyllactose (6'-SL), lacto-N-triose 2, (LNT-2), lacto-N-neotetraose (LNnT) and lacto-N-tetraose (LNT), but not for larger oligosaccharide structures, like pentasaccharides and hexasaccharides, which accumulate inside of the producing cells. Surprisingly, it is also found that the total production of the major HMO, e.g. 2'-fucosyllactose (2'-FL), 3'-fucosyllactose (3'-FL), lacto-N-triose, (LNT II) and lacto-N-tetraose (LNT), in the corresponding HMO producing cells expressing marc gene is also increased, while the by-product production, e.g. di-fucosyllactose (DFL), lacto-N-fucopentaose V (LNFP V) or para-lacto-neo-hexaose-I (pLNH-I), in these cells, correspondingly, is often decreased and said by-product oligosaccharides typically accumulate inside of the production cells. Further, highly unexpectedly, expression of Marc protein in HMO producing cells leads to reduction in formation of the biomass during fermentation and to healthier cell cultures reflected by reduction in the number of dead cells at the end of fermentation, which makes the manufacturing process more efficient as more product is produced per biomass unit.

Accordingly, a first aspect of the invention relates to a genetically modified cell capable of producing one or more HMO, wherein said cell comprises a recombinant nucleic acid encoding a protein of SEQ ID NO: 1, or a functional homologue thereof which amino acid sequence is at least 80% identical, preferably at least 85% identical, more preferably at least 90% identical to SEQ ID NO: 1.

A second aspect of the invention relates to a nucleic acid construct comprising a nucleic acid sequence(s) encoding an MFS transporter protein, wherein the nucleic acid sequence encoding the protein has at least 70% sequence identity to SEQ ID NO: 2, such as at least 80%, such as at least 85%, such as at least 95%, such as at least 99%, as well as to a genetically modified cell comprising the nucleic acid construct, which is *Escherichia coli*.

In one aspect, the nucleic acid construct comprises a nucleic acid sequence(s) encoding an MFS transporter protein, wherein the nucleic acid sequence is at least 70% identical to SEQ ID NO: 2.

A third aspect of the invention relates to a method for the production of one or more oligosaccharide, the method comprising the steps of:

(i) providing a genetically modified cell capable of producing an HMO, wherein said cell comprises a recombinant nucleic acid encoding a protein of SEQ ID NO: 1, or a functional homologue thereof which amino acid sequence is at least 80% identical, preferably at least 85% identical, more preferably at least 90% identical to SEQ ID NO: 1;

(ii) culturing the cell according to (i) in a suitable cell culture medium to express said recombinant nucleic acid;

(iii) harvesting one or more HMOs produced in step (ii).

The invention also relates to the use of a genetically modified cell or a nucleic acid construct comprising a heterologous nucleic acid sequence encoding a Major facilitator superfamily (MFS) protein, said nucleic acid sequence having at least 70% sequence identity to SEQ ID NO: 2, for the production of one or more Human Milk Oligosaccharides (HMOs).

As mentioned above, during the culturing of genetically modified cells capable of producing one or more HMOs, which cells comprise a nucleic acid encoding Marc transporter protein, it has surprisingly been found that the corresponding one or more HMOs are produced in high yields, while by-product and biomass formation is reduced. This facilitates recovery of the HMOs during downstream processes, e.g. the overall recovery and purification procedure may comprise less steps and overall time of purification may be shortened.

These effects of increased product yields and facilitation of the product recovery makes the present invention superior to the disclosures of the prior art.

Other aspects and advantageous features of the present invention are described in detail and illustrated by non-limiting working examples below.

BRIEF DESCRIPTION OF FIGURES

FIG. 3 presents SEQ ID NO: 1.

DETAILED DESCRIPTION

Figure 1:
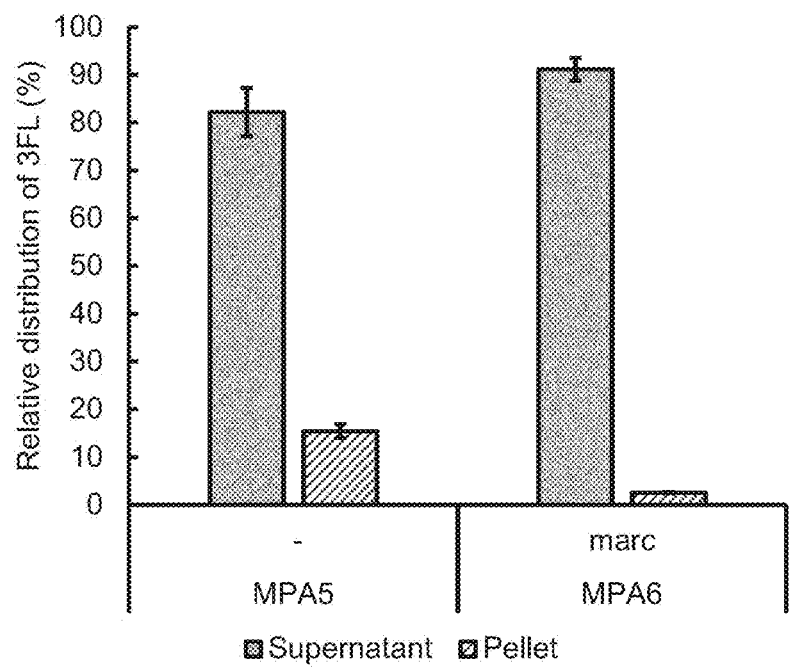
FIG. 1 shows the relative distribution of 3'-FL inside and outside the cells (FIG. 1) of a modified *E. coli* with and without the overexpression of the MFS transporter protein with SEQ ID NO: 1.

In the following, embodiments of the invention will be described in further detail. Each specific variation of the features can be applied to other embodiments of the invention unless specifically stated otherwise.

Generally, all terms used herein are to be interpreted according to their ordinary meaning in the technical field, and applicable to all aspects and embodiments of the invention, unless explicitly defined or stated otherwise. All references to "a/an/the [cell, sequence, gene, transporter, step, etc]" are to be interpreted openly as referring to at least one instance of said cell, sequence, gene, transporter, step, etc., unless explicitly stated otherwise. The steps of any method disclosed herein do not have to be performed in the exact order disclosed, unless explicitly stated.

The present invention in general relates to a genetically modified cell for efficient production of oligosaccharides and use of the said genetically modified cell in a method of producing the oligosaccharides. In particular, the present invention relates to a genetically modified cell enabled to synthesise an oligosaccharide, preferably a heterologous oligosaccharide, in particular a human milk oligosaccharide (HMO). Accordingly, a cell of the invention is modified to express a set of recombinant nucleic acids that are necessary for synthesis of one or more HMOs by the cells (which enable the cell to synthesise one or more HMOs), such as genes encoding one or more enzymes with glycosyltransferase activity described below. The oligosaccharide producing recombinant cell of the invention is further modified to comprise a heterologous recombinant nucleic acid sequence, preferably, a DNA sequence, encoding a putative MFS (major facilitator superfamily) transporter protein, originating from the bacterium *Serratia marcescens*. More specifically, the invention relates to a genetically modified cell optimized for the production of one or more particular oligosaccharides, in particular one or more particular HMOs, comprising a recombinant nucleic acid encoding a protein having at least 80% sequence similarity, preferably at least 85%, more preferably at least 90%, and even more preferably at least 95% sequence similarity to the amino acid sequence of SEQ ID NO: 1 (FIG. 3). The amino acid sequence identified herein as SEQ ID NO: 1 is an amino acid sequence that has 100% identity with the amino acid sequence having the GenBank accession ID: WP_060448169.1.

Accordingly, a first aspect of the invention relates to a genetically modified cell capable of producing one or more HMOs, wherein said cell comprises a recombinant nucleic acid encoding a protein of SEQ ID NO: 1, or a functional homologue thereof which amino acid sequence is at least 80% identical, preferably at least 85% identical, more preferably at least 90% identical to SEQ ID NO: 1. By the term "functional homolog" in the present context is meant a protein that has an amino acid sequence that is 80%-99.9% identical to SEQ ID NO: 1 and has a function that is beneficial to achieve at least one advantageous effect of the invention, e.g. an increase the total HMO production by the host cells, facilitate recovery of the produced HMO(s), HMO production efficiency and/or viability of an HMO producing cells.

The MFS transporter protein having the amino acid sequence of SEQ ID NO: 1 is identified herein as "Marc protein" or "Marc transporter" or "Marc", interchangeably; a nucleic acid sequence encoding Marc protein is identified here for the purposes of the invention in as "Marc coding nucleic acid/DNA" or "marc gene" or "marc".

By the term "Major Facilitator Superfamily (MFS)" is meant a large and exceptionally diverse family of the secondary active transporter class, which is responsible for transporting a range of different substrates, including sugars, drugs, hydrophobic molecules, peptides, organic ions, etc. The specificity of sugar transporter proteins is highly unpredictable and the identification of novel transporter protein with specificity towards for example oligosaccharides requires unburden laboratory experimentation (for more details see review by Reddy V. S. et al., (2012), FEBS J. 279(11): 2022-2035). The term "MFS transporter" means in the present context protein that facilitates transport of an oligosaccharide, preferably, an HMO, through the cell membrane, preferably transport of an HMO/oligosaccharide synthesized by the host cell from the cell cytosol to the cell medium, preferably an HMO/oligosaccharide comprising three or four sugar units, in particular, 2'-FL, 3'-FL, LNT-2, LNT, LNnT, 3'-SL or 6'-SL. Additionally, or alternatively, the MFS transporter, may also facilitate efflux of molecules which are not considered HMO or oligosaccharides according to the present invention, such as lactose, glucose, cell metabolites or toxins.

The term "sequence identity of [a certain] %" in the context of two or more nucleic acid or amino acid sequences means that the two or more sequences have nucleotides or amino acid residues in common in the given percent when compared and aligned for maximum correspondence over a comparison window or designated sequences of nucleic acids or amino acids (i.e. the sequences have at least 90 percent (%) identity). Percent identity of nucleic acid or amino acid sequences can be measured using a BLAST 2.0 sequence comparison algorithm with default parameters, or by manual alignment and visual inspection (see e.g. http://www.ncbi.nlm.nih.gov/BLAST/). This definition also applies to the complement of a test sequence and to sequences that have deletions and/or additions, as well as those that have substitutions. An example of an algorithm that is suitable for determining percent identity, sequence similarity and for alignment is the BLAST 2.2.20+ algorithm, which is described in Altschul et al. Nucl. Acids Res. 25, 3389 (1997). BLAST 2.2.20+ is used to determine percent sequence identity for the nucleic acids and proteins of the invention. Software for performing BLAST analyses is publicly available through the National Center for Biotechnology Information (http://www.ncbi.nlm.nih.gov/). Examples of commonly used sequence alignment algorithms are CLUSTAL Omega (http://www.ebi.ac.uk/Tools/msa/clustalo/), EMBOSS Needle (http://www.ebi.ac.uk/Tools/psa/emboss needle/), MAFFT (http://mafft.cbrc.jp/alignment/server/), or MUSCLE (http://www.ebi.ac.uk/Tools/msa/muscle/).

In the context of the invention, the term "oligosaccharide" means a saccharide polymer containing a number of monosaccharide units. In some embodiments, preferred oligosaccharides are saccharide polymers consisting of three or four monosaccharide units, i.e. trisaccharides or tetrasaccharides. Preferable oligosaccharides of the invention are human milk oligosaccharides (HMOs).

The term "human milk oligosaccharide" or "HMO" in the present context means a complex carbohydrate found in human breast milk (for reference, see Urashima et al.: *Milk Oligosaccharides*. Nova Science Publisher (2011); or Chen, *Adv. Carbohydr. Chem. Biochem.* 72, 113 (2015)). The HMOs have a core structure comprising a lactose unit at the reducing end that can be elongated by one or more beta-N-acetyl-lactosaminyl and/or one or more beta-lacto-N-biosyl units, and this core structure can be substituted by an alpha-L-fucopyranosyl and/or an alpha-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose 2 (LNT-2) lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-1), lacto-N-difucohexaose I (LNDFH-1), 3-fucosyllactose (3'-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), 3'-O-sialyllacto-N-tetraose a (LST a), fucosyl-LST a (FLST a), 6'-O-sialyllacto-N-tetraose b (LST b), fucosyl-LST b (FLST b), 6'-O-sialyllacto-N-neotetraose (LST c), fucosyl-LST c (FLST c), 3'-O-sialyllacto-N-neotetraose (LST d), fucosyl-LST d (FLST d), sialyl-lacto-N-hexaose (SLNH), sialyl-lacto-N-neohexaose I (SLNH-1), sialyl-lacto-N-neohexaose II (SLNH-II) and disialyl-lacto-N-tetraose (DSLNT). In the context of the present invention lactose is not regarded as an HMO species.

In some embodiments of the invention, tri-HMOs and tetra-HMOs may be a preferred, e.g. trisaccharides 2'-FL, 3'-FL, LNT-2, 3'-SL, 6'-SL, and tetrasaccharides DFL, LNT, LNnT, FSL.

To be able to synthesize one or more HMOs, the recombinant cell of the invention comprises at least one recombinant nucleic acid which encodes a functional enzyme with glycosyltransferase activity. The galactosyltransferase gene may be integrated into the genome (by chromosomal integration) of the host cell, or alternatively, it may be comprised in a plasmid DNA and expressed as plasmid-borne. If two or more glycosyltransferases are needed for the production of an HMO, e.g. LNT or LNnT, two or more recombinant nucleic acids encoding different enzymes with glycosyltransferase activity may be integrated in the genome and/or expressed from a plasmid, e.g. a beta-1,3-N-acetylglucosaminyltransferase (a first recombinant nucleic acid encoding a first glycosyltransferase) in combination with a beta-1,3-galactosyltransferase (a second recombinant nucleic acid encoding a second glycosyltransferase) for the production of LNT, where the first and second recombinant nucleic acid can independently from each other be integrated chromosomally or on a plasmid. In one preferred embodiment, both the first and second recombinant nucleic acids are stably integrated into the chromosome of the production cell; in another embodiment at least one of the first and second glycosyltransferase is plasmid-borne. A protein/enzyme with glycosyltransferase activity (glycosyltransferase) may be selected in different embodiments from enzymes having the activity of alpha-1,2-fucosyltransferase, alpha-1,3-fucosyltransferase, alpha-1,3/4-fucosyltransferase, alpha-1,4-fucosyltransferase alpha-2,3-sialyltransferase, alpha-2,6-sialyltransferase, beta-1,3-N-acetylglucosaminyltransferase, beta-1,6-N-acetylglucosaminyltransferase, beta-1,3-galactosyltransferase and beta-1,4-galactosyltransferase. For example, the production of 2'-FL requires that the modified cell expresses an active alpha-1,2-fucosyltransferase enzyme; for the production of 3'-FL the modified cell needs expression of an active alpha-1,3-fucosyltransferase enzyme; for the production of LNT the modified cell need to express at least two glycosyltransferases, a beta-1,3-N-acetylglucosaminyltransferase and a beta-1,3-galactosyltransferase; for the production of 6'-SL the modified cell has to express an active alpha-2,6-sialyltransferase enzyme. Some non-limiting embodiments of proteins having glycosyltransferase activity, which can be encoded by the recombinant genes comprised by the production cell, can be selected from non-limiting examples of Table 1.

TABLE 1

| Gene | Protein Sequence ID (GenBank) | Description | HMO example |
|---|---|---|---|
| lgtA_Nm | WP_002248149.1 | ββ-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Nm_MC58 | AAF42258.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Hd | AAN05638.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Ng_PID2 | AAK70338.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Ng_NCCP11945 | ACF31229.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Past | AAK02595.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Nc | EEZ72046.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |
| lgtA_Nm_87255 | ELK60643.1 | β-1,3-N-acetylglucosaminyltransferase | LNT, LNnT, LNFP-I, LNFP-II, LNFP-III, LNFP-V, LNFP-VI, LNDFH-I, LNDFH-II, pLNH, F-pLNH I, pLNnH |

TABLE 1-continued

| Gene | Protein Sequence ID (GenBank) | Description | HMO example |
|---|---|---|---|
| galT_Hp/ HP0826 | NP_207619.1 | ββ-1,4-galactosyltransferase | LNnT, LNFP-III, LNFP-VI, pLNH I, F-pLNH I, pLNnH |
| galT_Nm/ lgtB | AAF42257.1 | β-1,4-galactosyltransferase | LNnT, LNFP-III, LNFP-VI, pLNH I, F-pLNH I, pLNnH |
| wbgO | WP_000582563.1 | β-1,3-galactosyltransferase | LNT, LNFP-I, LNFP-II, LNFP-V, LNDFH-I, LNDFH-II, pLNH, F-pLNH I |
| cpslBJ | ABO50723.1 | ββ-1,3-galactosyltransferase | LNT, LNFP-I, LNFP-II, LNFP-V, LNDFH-I, LNDFH-II, pLNH, F-pLNH I |
| jhp0563 | AEZ55696.1 | β-1,3-galactosyltransferase | LNT, LNFP-I, LNFP-II, LNFP-V, LNDFH-I, LNDFH-II, pLNH, F-pLNH I |
| galTK | homologous to BD182026 | β-1,3-galactosyltransferase | LNT, LNFP-I, LNFP-II, LNFP-V, LNDFH-I, LNDFH-II, pLNH, F-pLNH I |
| futC | WP_080473865.1 | α-1,2-fucosyltransferase | 2'-FL, DFL, LNFP-I, LNDFH-I |
| FucT2_HpUA802 | AAC99764.1 | α-1,2-fucosyltransferase | 2'-FL, DFL, LNFP-I, LNDFH-I |
| FucT2_EcO126t | ABE98421.1 | α-1,2-fucosyltransferase | 2'-FL, DFL, LNFP-I, LNDFH-I |
| FucT2_Hm12198 | CBG40460.1 | α-1,2-fucosyltransferase | 2'-FL, DFL, LNFP-I, LNDFH-I |
| FucT2_Pm9515 | ABM71599.1 | α-1,2-fucosyltransferase | 2'-FL, DFL, LNFP-I, LNDFH-I |
| FucT2_HpF57 | BAJ59215.1 | α-1,2-fucosyltransferase | 2'-FL, DFL, LNFP-I, LNDFH-I |
| FucT6_3_Bf | CAH09151.1 | α-1,3-fucosyltransferase | 2'-FL, 3'-FL, DFL, LNFP-I, LNFP-III, LNFP-V, LNFP-VI, LNDFH-II, F-pLNH I |
| FucT7_3_Bf | CAH09495.1 | α-1,3-fucosyltransferase | 2'-FL, 3'-FL, DFL, LNFP-I, LNFP-III, LNFP-V, LNFP-VI, LNDFH-II, F-pLNH I |
| FucT_3_Am | ACD04596.1 | α-1,3-fucosyltransferase | 2'-FL, 3'-FL, DFL, LNFP-I, LNFP-III, LNFP-V, LNFP-VI, LNDFH-II, F-pLNH I |
| MAMA_R764 | AGC02224.1 | α-1,3-fucosyltransferase | 2'-FL, 3'-FL, DFL, LNFP-I, LNFP-III, LNFP-V, LNFP-VI, LNDFH-II, F-pLNH I |
| Mg791 | AEQ33441.1 | α-1,3-fucosyltransferase | 2'-FL, 3'-FL, DFL, LNFP-I, LNFP-III, LNFP-V, LNFP-VI, LNDFH-II, F-pLNH I |
| Moumou_00703 | YP_007354660 | α-1,3-fucosyltransferase | 2'-FL, 3'-FL, DFL, LNFP-I, LNFP-III, LNFP-V, LNFP-VI, LNDFH-II, F-pLNH I |
| futA | NP_207177.1 | α-1,3-fucosyltransferase | 2'-FL, 3'-FL, DFL, LNFP-I, LNFP-III, LNFP-V, LNFP-VI, LNDFH-II, F-pLNH I |
| fucT | AAB81031.1 | α-1,3-fucosyltransferase | 2'-FL, 3'-FL, DFL, LNFP-I, LNFP-III, LNFP-V, LNFP-VI, LNDFH-II, F-pLNH I |
| fucTIII | AY450598.1 | α-1,4-fucosyltransferase | LNDFH-I, LNDFH-II |
| fucTa | AF194963.1 | α-1,3/4-fucosyltransferase | LNFP-II, LNDFH-I, LNDFH-II |
| Pd2,6ST | BAA25316.1 | α-2,6-sialyltransferase | 6'-SL |
| PspST6 | BAF92026.1 | α-2,6-sialyltransferase | 6'-SL |
| PiST6_145 | BAF91416.1 | α-2,6-sialyltransferase | 6'-SL |

TABLE 1-continued

| Gene | Protein Sequence ID (GenBank) | Description | HMO example |
|---|---|---|---|
| PiST6_119 | BAI49484.1 | α-2,6-sialyltransferase | 6'-SL |
| NST | AAC44541.1 | α-2,3-sialyltransferase | 3'-SL |

An aspect of the present invention is the provision of a nucleic acid construct comprising a heterologous nucleic acid sequence(s) encoding a protein capable of sugar transportation which is a major facilitator superfamily (MFS) protein as shown in SEQ ID NO: 1, or a functional homologue thereof which amino acid sequence is at least 80% identical to SEQ ID NO: 1, wherein the nucleic acid sequence encoding the MFS protein has at least 70% sequence identity to SEQ ID NO: 2.

By the term "heterologous nucleic acid sequence", "recombinant gene/nucleic acid/DNA encoding" or "coding nucleic acid sequence" is meant an artificial nucleic acid sequence (i.e. produced in vitro using standard laboratory methods for making nucleic acid sequences) that comprises a set of consecutive, non-overlapping triplets (codons) which is transcribed into mRNA and translated into a polypeptide when placed under the control of the appropriate control sequences, i.e. promoter. The boundaries of the coding sequence are generally determined by a ribosome binding site located just upstream of the open reading frame at the 5'end of the mRNA, a transcriptional start codon (AUG, GUG or UUG), and a translational stop codon (UAA, UGA or UAG). A coding sequence can include, but is not limited to, genomic DNA, cDNA, synthetic, and recombinant nucleic acid sequences. The term "nucleic acid" includes RNA, DNA and cDNA molecules. It is understood that, as a result of the degeneracy of the genetic code, a multitude of nucleotide sequences encoding a given protein may be produced. The term nucleic acid is used interchangeably with the term "polynucleotide". An "oligonucleotide" is a short chain nucleic acid molecule. "Primer" is an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification but may alternatively be double stranded. If double stranded, the primer is first treated to separate its strands before being used to prepare extension products. Preferably, the primer is a deoxyribonucleotide. The primer must be sufficiently long to prime the synthesis of extension products in the presence of the inducing agent. The exact lengths of the primers will depend on many factors, including temperature, source of primer and the use of the method.

The recombinant nucleic sequence of the invention may be a coding DNA sequence, e.g. a gene, or non-coding DNA sequence, e.g. a regulatory DNA, such as a promoter sequence. One aspect of the invention relates to providing a recombinant cell comprising recombinant DNA sequences encoding enzymes necessary for the production of one or more HMOs and a DNA sequence encoding Marc protein. Accordingly, in one embodiment the invention relates to a nucleic acid construct comprising a coding nucleic sequence, i.e. recombinant DNA sequence of a gene of interest, e.g. a glycosyltransferase gene or the marc gene, and a non-coding DNA sequence, e.g. a promoter DNA sequence, e.g. a recombinant promoter sequence derived from the promoter of lac operon or an glp operon, or a promoter sequence derived from another genomic promoter DNA sequence, or a synthetic promoter sequence, wherein the coding and promoter sequences are operably linked. The term "operably linked" refers to a functional relationship between two or more nucleic acid (e.g., DNA) segments. Typically, it refers to the functional relationship of a transcriptional regulatory sequence to a transcribed sequence. For example, a promoter sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting.

In one embodiment, the nucleic acid construct of the invention may be a part of the vector DNA, in another embodiment the construct it is an expression cassette/cartridge that is integrated in the genome of a host cell. Accordingly, the term "nucleic acid construct" means an artificially constructed segment of nucleic acid, in particular a DNA segment, which is intended to be 'transplanted' into a target cell, e.g. a bacterial cell, to modify expression of a gene of the genome or express a gene/coding DNA sequence which may be included in the construct. In the context of the invention, the nucleic acid construct contains a recombinant DNA sequence comprising two or more recombinant DNA sequences: essentially, a non-coding DNA sequence comprising a promoter DNA sequence and a coding DNA sequence encoding a gene of interest, e.g. Marc protein, a glycosyltransferase, of another gene useful for production of an HMO in a host cell. Preferably, the construct comprises further non-coding DNA sequences that either regulate transcription or translation of the coding DNA of the construct, e.g. a DNA sequence facilitating ribosome binding to the transcript, a leading DNA sequence that stabilize the transcript.

Integration of the recombinant gene of interest comprised in the construct (expression cassette) into the bacterial genome can be achieved by conventional methods, e.g. by using linear cartridges that contain flanking sequences homologous to a specific site on the chromosome, as described for the attTn7-site (Waddell C. S. and Craig N. L., *Genes Dev.* (1988) February; 2(2):137-49.); methods for genomic integration of nucleic acid sequences in which recombination is mediated by the Red recombinase function of the phage λ or the RecE/RecT recombinase function of the Rac prophage (Murphy, *J Bacteriol.* (1998); 180(8): 2063-7; Zhang et al., *Nature Genetics* (1998) 20: 123-128 Muyrers et al., *EMBO Rep.* (2000) 1(3): 239-243); methods based on Red/ET recombination (Wenzel et al., *Chem Biol.*

(2005), 12(3):349-56.; Vetcher et al., *Appl Environ Microbiol.* (2005); 71(4):1829-35); or positive clones, i.e. clones that carry the expression cassette, can be selected e.g. by means of a marker gene, or loss or gain of gene function.

A single copy of the expression cassette comprising a gene of interest may be sufficient to secure production of a desired HMO and achieve the desired effects according to the invention. Accordingly, in some preferred embodiments, the invention relates to a recombinant HMO producing cell that comprises one, two or three copies of a gene of interest integrated in the genomic DNA of the cell. In some embodiments the single copy of the gene is preferred.

In one preferred embodiment, recombinant coding nucleic acid sequence of the nucleic acid construct of the invention is heterologous with respect to the promoter, which means that in the equivale native coding sequence in the genome of species of origin is transcribed under control of another promoter sequence (i.e. not the promoter sequence of the construct). Still, with respect to the host cell, the coding DNA may be either heterologous (i.e. derived from another biological species or genus), such as e.g. the DNA sequence encoding Marc protein expressed in *Escherichia coli* host cells, or homologous (i.e. derived from the host cell), such as e.g. genes of the colonic acid operon, the wca genes.

The term, a "regulatory element" or "promoter" or "promoter region" or "promoter element" is a nucleic acid sequence that is recognized and bound by a DNA dependent RNA polymerase during initiation of transcription. The promoter, together with other transcriptional and translational regulatory nucleic acid sequences (also termed "control sequences") is necessary to express a given gene or group of genes (an operon). In general, the transcriptional and translational regulatory sequences include, but are not limited to, promoter sequences, ribosomal binding sites, transcriptional start and stop sequences, translational start and stop sequences, and enhancer or activator sequences. The "transcription start site" means the first nucleotide to be transcribed and is designated +1. Nucleotides downstream of the start site are numbered +2, +3, +4 etc., and nucleotides in the 5' opposite (upstream) direction are numbered −1, −2, −3 etc. The promoter DNA sequence of the construct can derive from a promoter region of any gene of the genome of a selected species, preferably, a promoter region of the genomic DNA of *E. coli*. Accordingly, any promoter DNA sequence that is able to bind to an RNA polymerase and initiate transcription is suitable for practicing the invention. In principle, any promoter DNA sequence can be used to control transcription of the recombinant gene of interest of the construct, different or same promoter sequences may be used to drive transcription of different genes of interest integrated in the genome of the host cell or in expression vector DNA. To have an optimal expression of the recombinant genes included in the construct, the construct may comprise further regulatory sequences, e.g. a leading DNA sequence, such as a DNA sequence derived from 5'-untranslated region (5'UTR) of a glp gene of *E. coli*, a sequence for ribosomal binding. Examples of the later sequences are described in WO2019123324 (incorporated herein by reference) and illustrated in non-limiting working examples herein.

In some preferred embodiments, the regulatory element for the regulation of the expression of a recombinant gene included in the construct of the invention is glpFKX operon promoter, PlipF, in other preferred embodiments, the promoter is lac operon promoter, Plac.

In a further aspect the regulatory element for the regulation of the expression of a recombinant gene included in the construct of the invention is the mg/BAC; galactose/methylgalactosidade transporter promoter PmglB or variants thereof such as but not limited to PmglB_70UTR of SEQ ID NO: 12, or PmglB_70UTR_SD4 of SEQ ID NO: 13.

In a further aspect the regulatory element for the regulation of the expression of a recombinant gene included in the construct of the invention is the gatYZABCD; tagatose-1, 6-bisP aldolase promoter PgatY or variants thereof such as but not limited to PgatY_U70UTR of SEQ ID NO: 14.

The preferred regulatory element present in a genetically modified cell or in a nucleic acid construct of the present invention, is selected from the group consisting of PgatY_70UTR, PglpF, PglpF_SD1, PglpF_SD10, PglpF_SD2, PglpF_SD3, PglpF_SD4, PglpF_SD5, PglpF_SD6, PglpF_SD7, PglpF_SD8, PglpF_SD9, Plac_16UTR, Plac, PmglB_70UTR and PmglB_70UTR_SD4.

An especially preferred regulatory element present in a genetically modified cell or in a nucleic acid construct of the present invention, is selected from the group consisting of PglpF and Plac.

However, any promoter enabling transcription and/or regulation of the level of transcription of one or more recombinant nucleic acids that encode one or more proteins (or one or more regulatory nucleic acids) that are either necessary or beneficial to achieve an optimal level of biosynthetic production of one or more HMOs in the host cell, e.g. proteins involved in transmembrane transport of HMO, or HMO precursors, degradation of by-products of the HMO production, gene expression regulatory proteins, etc, and allowing to achieve the desired effects according to the invention is suitable for practicing the invention.

Preferably, the construct of the invention comprising a gene related to biosynthetic production of an HMO, a promoter DNA sequence, and other regulatory sequences, such as a ribosomal binding site sequence (e.g. Shine-Dalgarno sequence), expressed in the host cell enables production of the HMO at the level of at least 0.03 g/OD (optical density) of 1 liter of the fermentation media comprising a suspension of host cells, e.g., at the level of around 0.05 g/l/OD to around 0.1 g/l/OD. For the purposes of the invention, the later level of HMO production is regarded as "sufficient" and the host cell capable of producing this level of a desired HMO is regarded as "suitable host cell", i.e. the cell can be further modified to express the HMO transporter protein, e.g. Marc, to achieve at least one effect described herein that is advantageous for the HMO production.

The genetically modified cell or the nucleic acid construct of the present invention comprises a nucleic acid sequence such as a heterologous gene encoding a putative MFS (major facilitator superfamily) transporter protein.

A MFS transport protein of particular interest in the present invention is Marc protein. A nucleic acid construct of the present invention therefore contains a nucleic acid sequence having at least 70% sequence identity to the gene, marc, SEQ ID NO: 2.

The nucleic acid sequence contained in the genetically modified cell or in nucleic acid construct encodes for a protein of SEQ ID NO: 1, or a functional homologue thereof which amino acid sequence is at least 80% identical to SEQ ID NO: 1.

A functional homologue of the protein of SEQ ID NO: 1, may be obtained by mutagenesis. The functional homologue should have a remaining functionality of at least 50%, such as 60%, 70%, 80%, 90% or 100% compared to the functionality of amino acid sequence of SEQ ID NO: 1. The functional homologue can have a higher functionality compared to the functionality of amino acid sequence of SEQ ID NO: 1. The functional homologue of SEQ ID NO: 1, should be able to enhance HMO production of the genetically modified cell according to the invention.

The genetically modified cell (host cell or recombinant cell) may be e.g. a bacterial or yeast cell. In one preferred embodiment, the genetically modified bacterial cell. Regarding the bacterial host cells, there are, in principle, no limitations; they may be eubacteria (gram-positive or gram-negative) or archaebacteria, as long as they allow genetic manipulation for insertion of a gene of interest and can be cultivated on a manufacturing scale. Preferably, the host cell has the property to allow cultivation to high cell densities. Non-limiting examples of bacterial host cells that are suitable for recombinant industrial production of an HMO(s) according to the invention could be *Erwinia herbicola* (*Pantoea agglomerans*), *Citrobacter freundii*, *Pantoea citrea*, *Pectobacterium carotovorum*, or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus*, and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii,* and *Lactococcus lactis. Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and an oligosaccharide, such as an HMO, produced by the cell is retrieved, either from the bacterium itself or from a culture supernatant of the bacterium. In one preferred embodiment, the genetically modified cell of the invention is an *Escherichia coli* cell.

In another preferred embodiment the host cell is a yeast cell e.g. *Saccharomyces cerevisiae, Schizosaccharomyces pombe, Pichia pastoris, Kluveromyces lactis, Kluveromyces marxianus*, etc.

The HMOs produced by recombinant cells of the invention may be purified using a suitable procedure available in the art (e.g. such as described in WO2015188834, WO2017182965 or WO2017152918).

Genetically modified cells of the invention can be provided using standard methods of the art e.g. those described in the manuals by Sambrook et al., Wilson & Walker, "Maniatise et al, and Ausubel et al.

A host cell suitable for the HMO production, e.g. *E. coli*, may comprise an endogenous β-galactosidase gene or an exogenous β-galactosidase gene, e.g. *E. coli* comprises an endogenous lacZ gene (e.g., GenBank Accession Number V00296 (GI:41901)). For the purposes of the invention, an HMO-producing cell is genetically manipulated to either comprise any β-galactosidase gene or to comprise the gene that is inactivated. The gene may be inactivated by a complete or partial deletion of the corresponding nucleic acid sequence from the bacterial genome, or the gene sequence is mutated in the way that it is transcribed, or, if transcribed, the transcript is not translated or if translated to a protein (i.e. β-galactosidase), the protein does not have the corresponding enzymatic activity. In this way the HMO-producing bacterium accumulates an increased intracellular lactose pool which is beneficial for the production of HMOs.

In some embodiments, the engineered cell, e.g. bacterium, contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway described herein is the *E. coli* pathway. In this pathway, sialic acid (Neu5Ac; N-acetylneuraminic acid) is degraded by the enzymes NanA (N-acetylneuraminic acid lyase) and NanK (N-acetylmannosamine kinase) and NanE (N-acetylmannosamine-6-phosphate epimerase), all encoded from the nanATEK-yhcH operon, and repressed by NanR (http://ecocyc.org/ECOLI). A deficient sialic acid catabolic pathway is rendered in the *E. coli* host by introducing a mutation in the endogenous nanA (N-acetylneuraminate lyase) (e.g., GenBank Accession Number D00067.1 (GL216588)) and/or nanK (N-acetylmannosamine kinase) genes (e.g., GenBank Accession Number (amino acid) BAE77265.1 (GL85676015)), and/or nanE (N-acetylmannosamine-6-phosphate epimerase, GI: 947745, incorporated herein by reference). Optionally, the nanT (N-acetylneuraminate transporter) gene is also inactivated or mutated. Other intermediates of sialic acid metabolism include: (ManNAc-6-P)N-acetylmannosamine-6-phosphate; (GlcNAc-6-P)N-acetylglucosamine-6-phosphate; (GlcN-6-P) Glucosamine-6-phosphate, and (Fruc-6-P) Fructose-6-phosphate. In some preferred embodiments, nanA is mutated. In other preferred embodiments, nanA and nanK are mutated, while nanE remains functional. In another preferred embodiment, nanA and nanE are mutated, while nanK has not been mutated, inactivated or deleted. A mutation is one or more changes in the nucleic acid sequence coding the gene product of nanA, nanK, nanE, and/or nanT. For example, the mutation may be 1, 2, up to 5, up to 10, up to 25, up to 50 or up to 100 changes in the nucleic acid sequence. For example, the nanA, nanK, nanE, and/or nanT genes are mutated by a null mutation. Null mutations as described herein encompass amino acid substitutions, additions, deletions, or insertions, which either cause a loss of function of the enzyme (i.e. reduced or no activity) or loss of the enzyme (i.e. no gene product). By "deleted" is meant that the coding region is removed completely or in part such that no (functional) gene product is produced. By inactivated is meant that the coding sequence has been altered such that the resulting gene product is functionally inactive or encodes for a gene product with less than 100%, e.g. 90%, 80%, 70%, 60%, 50%, 40%, 30% or 20% of the activity of the native, naturally occurring, endogenous gene product. A "not mutated" gene or protein does not differ from a native, naturally-occurring, or endogenous coding sequence by 1, 2, up to 5, up to 10, up to 20, up to 50, up to 100, up to 200 or up to 500 or more codons, or to the corresponding encoded amino acid sequence.

Furthermore, the host cell (e.g., *E. coli*) also comprises a sialic acid synthetic capability. For example, the bacterium comprises a sialic acid synthetic capability through provision of an exogenous UDP-GlcNAc 2-epimerase (e.g., neuC of Campylobacterjejuni (GenBank AAK91727.1; GL15193223) or equivalent (e.g. neuC of *E. coli* S88

(GenBank YP_002392936.1; GI: 218560023), a Neu5Ac synthase (e.g., neuB of *C. jejuni* (GenBank AAK91726.1; GI:15193222) or equivalent, (e.g. *Flavobacterium limnosediminis* sialic acid synthase, GenBank GL559220424), and/or a CMP-Neu5Ac synthetase (e.g., neuA of *C. jejuni* (GenBank AAK91728.1; GI:15193224) or equivalent, (e.g. *Vibrio brasiliensis* CMP-sialic acid synthase, GenBank GI: 493937153).

Production of fucosylated HMOs in engineered yeasts is also known in the art (see e.g Yu et al., (2018) Microb Cell Fact 17:101; Hollands et al., (2019) Methabolic Eng 52:232-242)).

For the production of N-acetylglucosamine-containing HMOs, such as Lacto-N-triose 2 (LNT-2), Lacto-N-tetraose (LNT), Lacto-N-neotetraose (LNnT), Lacto-N-fucopentaose I (LNFP-1), Lacto-N-fucopentaose II (LNFP-II), Lacto-N-fucopentaose III (LNFP-Ill), Lacto-N-fucopentaose V (LNFP-V), Lacto-N-difucohexaose I (LDFH-1), Lacto-N-difucohexaose II (LDFH-II), and Lacto-N-neodifucohexaose II (LNDFH-III), the bacterium comprises a functional lacY and a dysfunctional lacZ gene, as described above, and it is engineered to comprise an exogenous UDP-GlcNAc:Galα/β-R-3-N-acetylglucosaminyltransferase gene (GlcNAcT), or a functional variant or fragment thereof. This exogenous UDP-GlcNAc:Galα/β-R-3-N-acetylglucosaminyltransferase gene may be obtained from any one of a number of sources,' (see Table 1) e.g., the lgtA gene described from *N. meningitidis* (Genbank protein Accession AAF42258.1) or *N. gonorrhoeae* (Genbank protein Accession ACF31229.1). Optionally, an additional exogenous glycosyltransferase gene may be co-expressed in the bacterium comprising an exogenous UDP-GlcNAc:Galα/β-R-3-N-acetylglucosaminyltransferase. For example, a beta-1,4-galactosyltransferase gene (Gal4T) is co-expressed with the UDP-GlcNAc:Galα/β-R-3-N-acetylglucosaminyltransferase gene. This exogenous beta-1,4-galactosyltransferase gene can be obtained from any one of a number of sources, e.g., the one described from *N. meningitidis*, the lgtB gene (Genbank protein Accession AAF42257.1), or from *H. pylori*, the HP0826/galT gene (Genbank protein Accession NP_207619.1). Optionally, the additional exogenous glycosyltransferase gene co-expressed in the bacterium comprising an exogenous UDP-GlcNAc:Galα/β-R-3-N-acetylglucosaminyltransferase gene is a β-1,3-galactosyltransferase gene (Gal3T), e.g., that described from *E. coli* O55:H7, the wbgO gene (Genbank protein Accession WP_000582563), or from *H. pylori*, the jhp0563 gene (Genbank protein Accession AEZ55696.1), or from *Streptococcus agalactiae* type Ib O12 the cpslBJ gene Genbank protein Accession AB050723). Functional variants and fragments of any of the enzymes described above are also encompassed by the disclosed invention.

A N-acetylglucosaminyltransferase gene and/or a galactosyltransferase gene, can also be operably linked to a Pglp and be expressed from the corresponding genome-integrated cassette. In one embodiment, the gene that is genome integrated is a gene encoding for a galactosyltransferase, e.g. HP0826 gene encoding for the GalT enzyme from *H. pylori* (Genbank protein Accession NP_207619.1); in another embodiment, the gene that is genome integrated is a gene encoding a β-1,3-N-acetylglucosaminyltransferase, e.g. lgtA gene from *N. meningitidis* (Genbank protein Accession AAF42258.1). In these embodiments, the second gene, i.e. a gene encoding a β-1,3-N-acetylglucosaminyltransferase or galactosyltransferase, correspondingly, may either be expressed from a genome-integrated or plasmid borne cassette. The second gene may optionally be expressed either under the control of a glp promoter or under the control of any other promoter suitable for the expression system, e.g. Plac.

Unless otherwise specified, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. Most of the nomenclature and general laboratory procedures required in this application can be found in Sambrook et al., Molecular Cloning: A Laboratory Manual, Vol. 1-3, Cold Spring Harbor Laboratory, Cold Spring Harbor, N.Y. (2012); Wilson K. and Walker J., Principles and Techniques of Biochemistry and Molecular Biology (2010), Cambridge University Press; or in Maniatise et al., Molecular Cloning A laboratory Manual, Cold Spring Harbor Laboratory (2012); or in Ausubel et al., Current protocols in molecular biology, John Wiley and Sons (2010). The manuals are hereinafter referred to as "Sambrook et al.", "Wilson & Walker", "Maniatise et al.", "Ausubel et al.", correspondingly.

A second aspect of the invention related to a method for the production of one or more HMOs, the method comprising the steps of:
  (i) providing a genetically modified cell capable of producing an HMO, wherein said cell comprises a recombinant nucleic acid encoding a protein of SEQ ID NO: 1, or a functional homologue thereof which amino acid sequence is at least 80% identical, preferably at least 85% identical, more preferably at least 90% identical to SEQ ID NO: 1;
  (ii) culturing the cell of (i) in a suitable cell culture medium to allow the HMO production and expression of the DNA sequence to produce the protein having the amino acid sequence of SEQ ID NO: 1; or a functional homologue thereof which amino acid sequence is at least 80% identical, preferably at least 85% identical, more preferably at least 90% identical to SEQ ID NO: 1;
  (iii) harvesting the HMO(s) produced in step (ii).

According to the invention, the term "culturing" (or "cultivating" or "cultivation", also termed "fermentation") relates to the propagation of bacterial expression cells in a controlled bioreactor according to methods known in the industry.

To produce one or more HMOs, the HMO-producing bacteria as described herein are cultivated according to the procedures known in the art in the presence of a suitable carbon source, e.g. glucose, glycerol, lactose, etc., and the produced HMO is harvested from the cultivation media and the microbial biomass formed during the cultivation process. Thereafter, the HMOs are purified according to the procedures known in the art, e.g. such as described in WO2015188834, WO2017182965 or WO2017152918, and the purified HMOs are used as nutraceuticals, pharmaceuticals, or for any other purpose, e.g. for research. Manufacturing of HMOs is typically accomplished by performing cultivation in larger volumes. The term "manufacturing" and "manufacturing scale" in the meaning of the invention defines a fermentation with a minimum volume of 5 L culture broth. Usually, a "manufacturing scale" process is defined by being capable of processing large volumes of a preparation containing the HMO or HMOs of interest and yielding amounts of the protein of interest that meet, e.g. in the case of a therapeutic compound or composition, the demands for clinical trials as well as for market supply. In addition to the large volume, a manufacturing scale method, as opposed to simple lab scale methods like shake flask cultivation, is characterized by the use of the technical system of a bioreactor (fermenter) which is equipped with devices for agitation, aeration, nutrient feeding, monitoring and control of process parameters (pH, temperature, dissolved oxygen tension, back pressure, etc.). To a large extent, the behavior of an expression system in a lab scale method, such as shake flasks, benchtop bioreactors or the deep well format described in the examples of the disclosure, does allow to predict the behavior of that system in the complex environment of a bioreactor.

With regard to the suitable cell cultivation medium used in the fermentation process, there are no limitations. The culture medium may be semi-defined, i.e. containing complex media compounds (e.g. yeast extract, soy peptone, casamino acids, etc.), or it may be chemically defined, without any complex compounds.

By the term "one or more HMOs" is meant that an HMO production cell may be able to produce a single HMO structure (a first HMO) or multiple HMO structures (a second, a third, etc. HMO). In some embodiments, it may be preferred a host cell that produces a single HMO, in other preferred embodiments, a host cell producing multiple HMO structures may be preferred. Non-limiting examples for host cells producing single HMO structures are 2'-FL, 3'-FL, 3'-SL, 6'-SL or LNT-2 producing cells. Non-limiting examples of host cells capable of producing multiple HMO structures can be DFL, FSL, LNT, LNnT, LNFP I, LNFP II, LNFP III, LNFP IV, LNFP V, pLNnH producing cells.

The term "harvesting" in the context in the invention relates to collecting the produced HMO(s) following the termination of fermentation. In different embodiments it may include collecting the HMO(s) included in both the biomass (i.e. the host cells) and cultivation media, i.e. before/without separation of the fermentation broth from the biomass. In other embodiments the produced HMOs may be collected separately from the biomass and fermentation broth, i.e. after/following the separation of biomass from cultivation media (i.e. fermentation broth). The separation of cells from the medium can be carried out with any of the methods well known to the skilled person in the art, such as any suitable type of centrifugation or filtration. The separation of cells from the medium can follow immediately after harvesting the fermentation broth or be carried out at a later stage after storing the fermentation broth at appropriate conditions. Recovery of the produced HMO(s) from the remaining biomass (or total fermentation) include extraction thereof from the biomass (i.e the production cells). It can be done by any suitable methods of the art, e.g. by sonication, boiling, homogenization, enzymatic lysis using lysozyme, or freezing and grinding.

After recovery from fermentation, HMO(s) are available for further processing and purification.

Purification of HMOs produced by fermentation can be done using a suitable procedure described in WO2016095924, WO2015188834, WO2017152918, WO2017182965, US20190119314 (all incorporated by reference).

In some embodiments of the invention, a host cell may produce several HMOs, wherein one HMO is the "product" HMO and some/all the other HMOs are "by-product" HMOs. Typically, by-product HMOs are either the major HMO precursors or products of further modification of the major HMO. In some embodiments, it may be desired to produce the product HMO in abundant amounts and by-product HMOs in minor amounts. Cells and methods for HMO production described herein allow for controlled production of an HMO product with a defined HMO profile, e.g. in one embodiment, the produced HMO mixture wherein the product HMO is a dominating HMO compared to the other HMOs (i.e. by-product HMOs) of the mixture, i.e. the product HMO is produced in higher amounts than other by-product HMOs; in other embodiments, the cell producing the same HMO mixture may be tuned to produce one or more by-product HMOs in higher amount than product HMO. For example, during the production of 3'-FL, the product HMO, often a significant amount of DFL, the by-product HMO, is produced. With the genetically modified cells of the present invention the level of DFL in the 3'-FL product can be significantly reduced.

Advantageously, the invention provides both a decreased ratio of by-product to product and an increased overall yield of the product (and/or HMOs in total). This, less by-product formation in relation to product formation facilitates an elevated product formation and increases efficiency of both the production and product recovery process, providing superior manufacturing procedure of HMOs.

In different preferred embodiments, different host cells producing either/both 2'-FL, 3'-FL, 3'-SL, 6'-SL, LNT-2, DFL, FSL, LNT, LNnT, DFL, FSL, LNT, LNnT, LNFP I, LNFP II, LNFP III, LNFP IV, LNFP V, pLNnH, as the product or by-product HMO, may be selected. In one preferred embodiment, the product is 3'-FL and the by-product is DFL. In another preferred embodiment, the product is 2'-FL and the by-product is DFL. In another preferred embodiment, the product is LNT-2, and the by-products are LNT and LNFP I.

The invention also relates to the use of a genetically modified cell and/or a nucleic acid construct according to the invention, for the production of one or more oligosaccharides, preferably one or more human milk oligosaccharide(s). In one embodiment, the genetically modified cell or the nucleic acid construct according to the invention is used in the production of a specific HMO selected from the group consisting of 2'-FL, 3-FL, DLF, LNT, LNT-II, LNnT, pLNnH and pLNH-II.

In an especially preferred embodiment, the genetically modified cell and/or the nucleic acid construct according to the invention is used in the production of a specific HMO selected from the group consisting of 2'-FL and 3-FL.

The invention is further illustrated by non-limiting examples and embodiments below.

EXAMPLES

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); Bukhari et al. (eds.), *DNA Insertion Elements, Plasmids and Episomes* (1977) (Cold Spring Harbor Laboratory Press, NY); Miller, J. H. Experiments in molecular genetics (1972.) (Cold spring Harbor Laboratory Press, NY)

The embodiments described below are selected to illustrate the invention and are not limiting the invention in any way.

Strains

The bacterial strain used, MDO, was constructed from *Escherichia coli* K12 DH1. The *E. coli* K12 DH1 genotype is: F−, λ−, gyrA96, recA1, relA1, endA1, thi-1, hsdR17, supE44. Strains utilized in the present Examples are described in Table 2.

TABLE 2

| Strain IDs | Product | Relevant Genotype |
|---|---|---|
| DH1 | — | F− λ− endA1 recA1 relA1 gyrA96 thi-1 glnV44 hsdR17($r_K^- m_K^-$) |
| MDO | — | *E coli* DH1 ΔlacZ, ΔlacA, ΔnanKETA, ΔmelA, ΔwcaJ, ΔmdoH |
| MPA7 | 2'-FL | MDO PglpF-CA ΔlacI PglpF-futC PglpF -marc |
| MPA1 | | MDO PglpF-CA ΔlacI PglpF-futC |
| MPA5 | 3'-FL | MDO PglpF-CA ΔlacI PglpF-futA |
| MPA6 | | MDO PglpF-CA ΔlacI PglpF-futA PglpF-marc |

Media

The Luria Broth (LB) medium was made using LB Broth Powder, Millers (Fisher Scientific) and LB agar plates were made using LB Agar Powder, Millers (Fisher Scientific). When appropriated ampicillin ((100 μg/mL) or any appropriated antibiotic), and/or chloramphenicol (20 μg/mL) was added.

Basal Minimal medium had the following composition: NaOH (1 g/L), KOH (2.5 g/L), $KH_2PO_4$ (7 g/L), $NH_4H_2PO_4$ (7 g/L), Citric acid (0.5 g/l), Trace mineral solution (5 mL/L). The trace mineral stock solution contained: $ZnSO_4 \cdot 7H_2O$ 0.82 g/L, Citric acid 20 g/L, $MnSO_4 \cdot H_2O$ 0.98 g/L, $FeSO_4 \cdot 7H_2O$ 3.925 g/L, $CuSO_4 \cdot 5H_2O$ 0.2 g/L. The pH of the Basal Minimal Medium was adjusted to 7.0 with 5 N NaOH and autoclaved. Before inoculation, the Basal Minimal medium was supplied with 1 mM $MgSO_4$, 4 μg/mL thiamin, 0.5% of a given carbon source (glycerol (Carbosynth)). Thiamin, and antibiotics, were sterilized by filtration. All percentage concentrations for glycerol are expressed as v/v and for glucose as w/v.

M9 plates containing 2-deoxy-galactose had the following composition: 15 g/L agar (Fisher Scientific), 2.26 g/L 5×M9 Minimal Salt (Sigma-Aldrich), 2 mM MgSO4, 4 μg/mL thiamine, 0.2% glycerol, and 0.2% 2-deoxy-D-galactose (Carbosynth).

MacConkey indicator plates had the following composition: 40 g/L MacConkey agar Base (BD Difco™) and a carbon source at a final concentration of 1

Cultivation

Unless otherwise noted, *E. coli* strains were propagated in Luria-Bertani (LB) medium containing 0.2% glucose at 37° C. with agitation. Agar plates were incubated at 37° C. overnight.

Chemical Competent Cells and Transformations

*E. coli* was inoculated from LB plates in 5 mL LB containing 0.2% glucose at 37° C. with shaking until OD600~0.4. 2 mL culture was harvested by centrifugation for 25 seconds at 13.000 g. The supernatant was removed and the cell pellet resuspended in 600 μL cold TB solutions (10 mM PIPES, 15 mM $CaCl_2$, 250 mM KCl). The cells were incubated on ice for 20 minutes followed by pelleting for 15 seconds at 13.000 g. The supernatant was removed and the cell pellet resuspended in 100 μL cold TB solution. Transformation of plasmids were done using 100 μL competent cells and 1 to 10 ng plasmid DNA. Cells and DNA were incubated on ice for 20 minutes before heat shocking at 42° C. for 45 seconds. After 2 min incubation on ice 400 μL SOC (20 g/L tryptone, 5 g/L Yeast extract, 0.5 g/L NaCl, 0.186 g/L KCl, 10 mM $MgCl_2$, 10 mM $MgSO_4$ and 20 mM glucose) was added and the cell culture was incubated at 37° C. with shaking for 1 hour before plating on selective plates.

Plasmid were transformed into TOP10 chemical competent cells at conditions recommended by the supplier (ThermoFisher Scientific).

DNA Techniques

Plasmid DNA from *E. coli* was isolated using the QIAprep Spin Miniprep kit (Qiagen). Chromosomal DNA from *E. coli* was isolated using the QIAmp DNA Mini Kit (Qiagen). PCR products were purified using the QIAquick PCR Purification Kit (Qiagen). DreamTaq PCR Master Mix (Thermofisher), Phusion U hot start PCR master mix (Thermofisher), USER Enzym (New England Biolab) were used as recommended by the supplier. Primers were supplied by Eurofins Genomics, Germany. PCR fragments and plasmids were sequenced by Eurofins Genomics. Colony PCR was done using DreamTaq PCR Master Mix in a T100™ Thermal Cycler (Bio-Rad).

TABLE 3

Oligos used for amplification of plasmid backbones, promoter elements, and marc

| Name | SEQ ID NO | Oligonucleotide Sequence 5'-3' | Description |
|---|---|---|---|
| O40 | 4 | ATTAACCCUCCAGGC ATCAAATAAAACGAA AGGC | Backbone.for |
| O79 | 5 | ATTTGCGCAUCACCA ATCAAATTCACGCGG CC | Backbone.rev |
| O261 | 6 | ATGCGCAAAUGCGGC ACGCCTTGCAGATTA CG | PglpF.for |
| O262 | 7 | AGCTGTTUCCTCCTT GGTTAATGTTTGTTG TATGCG | PglpF.rev |
| O737 | 8 | AAACAGCUATGCAGC GTCTGAGCCGTCTGA G | marc.for |
| O738 | 9 | AGGGTTAAUTTAAAC TTCACGCACTTTCGC GC | marc.rev |
| O48 | 10 | CCCAGCGAGACCTGA CCGCAGAAC | galK.for |
| O49 | 11 | CCCCAGTCCATCAGC GTGACTACC | galK.rev |

TABLE 4

The heterologous proteins expressed in the HMO-producing cells

| Gene | Origin of Genes | Protein GenBank Accession Number | Protein Function |
|---|---|---|---|
| futC | Helicobacter pylori 26695 | ABO61751.1 | alpha-1,2-fucosyl-transferase |
| futA | Helicobacter pylori 26695 | NP_207177.1 | alpha-1,3-fucosyl-transferase |
| marc | Serratia marcescens | WP_060448169.1 | MFS transporter |

TABLE 5

The synthetic DNA utilized for expression of marc

| Sequence name | SEQ ID NO | Sequence (5'-3') | Description |
|---|---|---|---|
| PglpF | 3 | GCGGCACGCCTTGCAGATTA CGGTTTGCCACACTTTTCAT CCTTCTCCTGGTGACATAAT CCACATCAATCGAAAATGTT AATAAATTTGTTGCGCGAAT GATCTAACAAACATGCATCA TGTACAATCAGATGGAATAA ATGGCGCGATAACGCTCATT TTATGACGAGGCACACACAT TTTAAGTTCGATATTTCTCG TTTTTGCTCGTTAACGATAA GTTTACAGCATGCCTACAAG CATCGTGGAGGTCCGTGACT TTCACGCATACAACAAACAT TAACCAAGGAGGAAACAGCT | 300-nucleotide DNA expression element |
| marc | 2 | ATGCAGCGTCTGAGCCGTCT GAGCCTGCGTATCAACCCGA TTTTCGCGGCGTTTCTGCTG ATCGCGTTCCTGAGCGGTAT TGCGGGTGCGCTGCTGACCC CGACCCTGAGCCTGTTTCTG ACCACCGAGGTGAAGGTTCG TCCGCTGTGGGTGGGTCTGT TCTACACCGCGAACGCGGTT GCGGGCATCGTGGTTAGCTT TCTGCTGGCGAAACGTAGCG ACACCCGTGGTGACCGTCGT CGTCTGATTCTGCTGTGCTG CCTGATGGCGGTGGGCAACT GCCTGCTGTTCGCGTTTAAC CGTGACTACCTGACCCTGAT CACCGCGGGTGTGCTGATGA GCGCGGTTGCGAACACCGCG ATGCCGCAGATTTTCGCGCT GGCGCGTGAATATGCGGATA GCGAGGCGCGTGAAGTGGTT ATGTTTAGCAGCGTGATGCG TGCGCAACTGAGCCTGGCGT GGGTTATTGGTCCGCCGCTG AGCTTCGCGCTGGCGCTGAA CTATGGCTTCACCGTGATGT TTCTGATTGCGGCGGTTACC TTCGCGGTGTGCGTTCTGCT GGTTGGTTTTATGCTGCCGA GCGTTCCGCGTGCGGCGGAG AACGAAGGCCTGCAGGGTGG CGTGAGCGCGCCGATTGCGC CGGCGAGCGCGTGGCGTAAC CGTGACGTTCGTCTGCTGTT TATTGCGAGCATGCTGATGT GGACCTGCAACACCCTGTAC ATCATTGACATGCCGCTGTA TATCACCGCGGATCTGGGTC TGCCGGAGGGTCTGGCGGGC GTGCTGATGGGCACCGCGGC GGGCCTGGAAATCCCGGCGA TGCTGCTGGCGGGTTACTAT GTTAAGCGTTTCGGCAAACG TAACATGATGCTGCTGGCGG TGGTTGCGGGTGTGCTGTTT TACCTGGGCCTGACCGTTCT GGAGAGCAAACCGGCGCTGA TTGCGCTGCAGCTGCTGAAC GCGGTGTTCATCGGTATTGT TGCGGGTATTGGCATGCTGT ATTTTCAGGACCTGATGCCG GGTCGTCCGGGTGCGGCGAC CACCCTGTTCACCAACAGCA TCAGCACCGGCGTGATTCTG GCGGGTGTTCTGCAAGGCGC GCTGGTTGAGAACCTGGGTC ACGGCAGCGTTTACTGGATG GCGGCGCTGCTGGCGCTGGC GGCGCTGGGTATGAGCGCGA AAGTGCGTGAAGTTTAA | MFS transporter |

Construction of Plasmids

Plasmid backbones containing two 1-SceI endonuclease sites, separated by two DNA fragments appropriated for homologous recombination into the E. coli genome and a T1 transcriptional terminator sequence were synthesized. For example, in one plasmid backbone the gal operon (required for homologous recombination in galK), and a T1 transcriptional terminator sequence (pUC57::gal) was synthesized (GeneScript). The DNA sequences used for homologous recombination in the gal operon covered base pairs 3.628.621-3.628.720 and 3.627.572-3.627.671 in sequence Escherichia coli K-12 MG155 complete genome GenBank: ID: CP014225.1. Insertion by homologous recombination would result in a deletion of 949 base pairs of galK and a galK– phenotype. In similar ways, backbones based on pUC57 (GeneScript) or an any other appropriated vector containing two 1-SceI endonuclease sites, separated by two DNA fragments appropriated for homologous recombination into the E. coli genome and a T1 transcriptional terminator sequence could be synthesized. Standard techniques well-known in the field of molecular biology were used for designing of primers and amplification of specific DNA sequences of the Escherichia coli K-12 DH1 chromosomal DNA. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); Bukhari et al. (eds.).

Chromosomal DNA obtained from E. coli DH1 was used to amplify a 300 bp DNA fragment containing the promoter PglpF using oligos O261 and O262 (Table 3).

A 1.197 bp DNA fragment containing a codon optimized version of the marc gene originating from Serratia marcescens was synthesized by GeneScript (Table 5). The marc gene was amplified by PCR using oligos O737 and O738 (Table 3).

All PCR fragments (plasmid backbones, promoter containing elements and the marc gene) were purified, and plasmid backbones, promoter element ( ), and a marc containing DNA fragment were assembled. The plasmids were cloned by standard USER cloning. Cloning in any appropriated plasmid could be done using any standard DNA cloning techniques. The plasmids were transformed into TOP10 cells and selected on LB plates containing 100 µg/mL ampicillin (or any appropriated antibiotic) and 0.2% glucose. The constructed plasmids were purified and the promoter sequence and the 5'end of the marc gene was verified by DNA sequencing (MWG Eurofins Genomics). In this way, a genetic cassette containing any promoter of interest linked to the marc gene was constructed.

Construction of Strains

The bacterial strain used, MDO, was constructed from *Escherichia coli* K-12 DH1. The *E. coli* K-12 DH1 genotype is: F⁻, λ⁻, gyrA96, recA1, re/A1, endA1, thi-1, hsdR17, supE44. In addition to the *E. coli* K-12 DH1 genotype MDO has the following modifications: lacZ: deletion of 1.5 kbp, lacA: deletion of 0.5 kbp, nanKETA: deletion of 3.3 kbp, me/A: deletion of 0.9 kbp, wcaJ: deletion of 0.5 kbp, mdoH: deletion of 0.5 kbp, and insertion of Plac promoter upstream of the gmd gene.

Insertion of an expression cassette containing a promoter linked to the marc gene and to a T1 transcriptional terminator sequence was performed by Gene Gorging essentially as described by Herring et al. (Herring, C. D., Glasner, J. D. and Blattner, F. R. (2003). Gene (311). 153-163). Briefly, the donor plasmid and the helper plasmid were co-transformed into MDO and selected on LB plates containing 0.2% glucose, ampicillin (100 µg/mL) or kanamycin (50 mg/mL) and chloramphenicol (20 µg/mL). A single colony was inoculated in 1 mL LB containing chloramphenicol (20 µg/mL) and 10 µL of 20% L-arabinose and incubated at 37° C. with shaking for 7 to 8 hours. For integration in the galK loci of *E. coli* cells were then plated on M9-DOG plates and incubated at 37° C. for 48 hours. Single colonies formed on MM-DOG plates were re-streaked on LB plates containing 0.2% glucose and incubated for 24 hours at 37° C. Colonies that appeared white on MacConkey-galactose agar plates and were sensitive for both ampicillin and chloramphenicol were expected to have lost the donor and the helper plasmid and contain an insertion in the galK loci. Insertions in the galK site was identified by colony PCR using primers O48 and O49 (Table 3) and the inserted DNA was verified by sequencing (Eurofins Genomics, Germany).

Insertion of genetic cassettes at other loci in the *E. coli* chromosomal DNA was done in a similar way using different selection marker genes.

Deep Well Assay (DWA)

DWA was performed as originally described to Lv et al (Bioprocess Biosyst Eng (2016) 39:1737-1747) and optimized for the purposes of the current invention. More specifically, the strains disclosed in the examples were screened in 24 deep well plates using a 4-day protocol. During the first 24 hours, cells were grown to high densities while in the next 72 hours cells were transferred to a medium that allowed induction of gene expression and product formation. Specifically, during day 1 fresh inoculums were prepared using a basal minimal medium supplemented with magnesium sulphate, thiamine and glucose. After 24 hours of incubation of the prepared cultures at 34° C. with a 700 rpm shaking, cells were transferred to a new basal minimal medium (2 ml) supplemented with magnesium sulphate and thiamine to which an initial bolus of 20% glucose solution (1 µl) and 10% lactose solution (0.1 ml) were added, then 50% sucrose solution as carbon source was provided to the cells. After inoculation of the new medium, cells were shaken at 700 rpm at 28° C. for 72 hours. After denaturation and subsequent centrifugation, the supernatants were analysed by HPLC.

For the analysis of total samples, the cell lysate prepared by boiling was pelleted by centrifugation for 10 minutes at 4.700 rpm. The HMO concentration in the supernatant was determined by HPLC or HPAC methods.

Results

Example 1. Engineering of *Escherichia Coli* for 3FL Production Expressing the Marc Gene The *Escherichia coli* K-12 (DH1) MDO strains can be manipulated to express heterologous genes of interest. For instance, the strain MPA5 is a 3FL production strain overexpressing the alpha-1,3-fucosyltransferase gene, futA, and the colonic acid genes (gmd-fcl-gmm-wcal-cpsB-cpsG). Insertion of an expression cassette containing a promoter element (PglpF) linked to a marc gene in a single copy into the MPA5 background strain resulted in strain MPA6 and i) relatively higher amounts of 3FL in the media fraction and ii) relative lower amounts of 3FL inside the cells (FIG. 1).

Figure 2A:
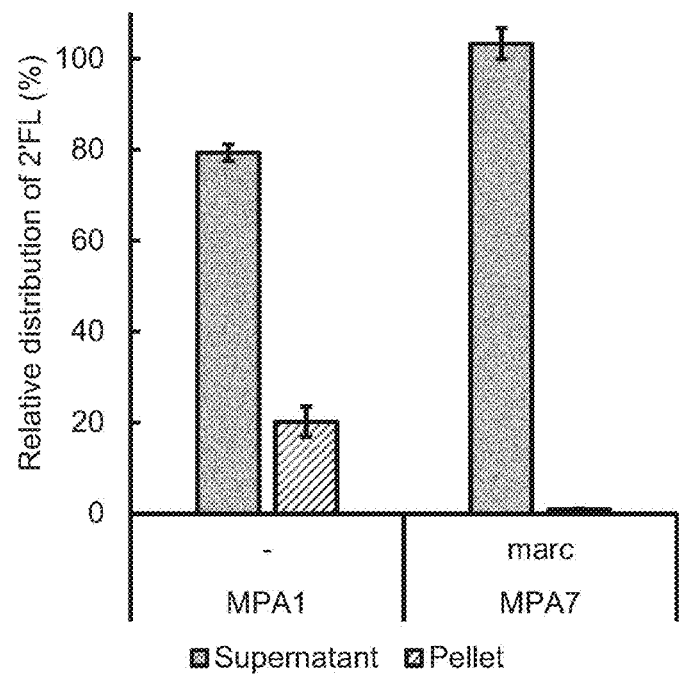
FIG. 2 shows the relative distribution of 2'FL inside and outside the cells (FIG. 2A), and the relative cell optical density measured at 600 nm (FIG. 2B) in modified *E. coli* with and without the overexpression of the MFS transporter protein with SEQ ID NO: 1.
Figure 2B:
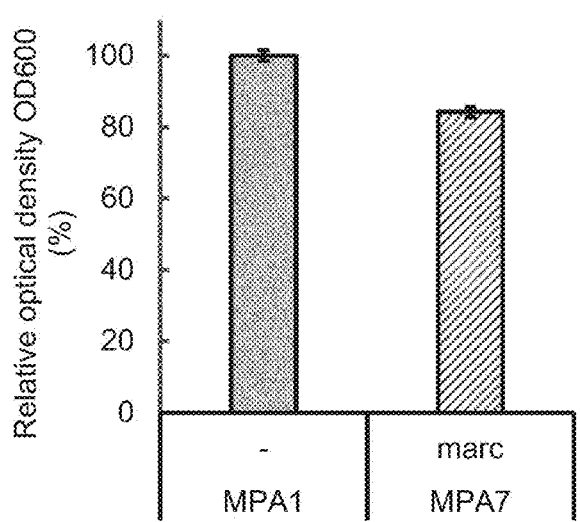

Example 2. Engineering of *Escherichia coli* for 2'FL Production Expressing the Marc Gene The *Escherichia coli* K-12 (DH1) MDO strains can be manipulated to express heterologous genes of interest. For instance, the strain MPA1 is a 2'FL production strain overexpressing the α-1,2-fucosyltransferase gene, futC, and the colonic acid genes (gmd-fcl-gmm-wcal-cpsB-cpsG). Insertion of an expression cassette containing a promoter element (PglpF) linked to a marc gene into the MPA1 chromosomal DNA resulted in strain MPA7 and i) relative higher amounts of 2'FL in the media fraction, ii) relative lower amounts of 2'FL inside the cells (FIG. 2A), and iii) relative lower optical density at 600 nm (FIG. 2B).

The invention claimed is:

1. A genetically modified cell capable of producing one or more Human Milk Oligosaccharides (HMOs), wherein the cell comprises a recombinant nucleic acid encoding a protein of SEQ ID NO: 1, or a functional homologue thereof with an amino acid sequence that is at least 95% identical to SEQ ID NO: 1.

2. The genetically modified cell according to claim 1, wherein the one or more HMOs are selected from the list of 2'-fucosyllactose (2'-FL), 3-fucosyllactose (3FL), difucosyllactose (DFL), 3'-sialyllactose (3'-SL), 6'-sialyllactose (6'-SL), Lacto-N-Triose-2 (LNT-2), Lacto-N-tetraose (LNT), Lacto-N-fucopentaose I (LNFP I), Lacto-N-fucopentaose II (LNFP II), Lacto-N-fucopentaose III (LNFP III), Lacto-N-fucopentaose IV (LNFP IV), and Lacto-N-fucopentaose V (LNFP V), and para-lacto-N-neohexaose (pLNnH); or a mixture thereof.

3. The genetically modified cell according to claim 1, wherein the genetically modified cell is *Escherichia coli*.

4. The genetically modified cell according to claim 1, wherein the cell further comprises a recombinant regulatory element comprising a nucleic acid sequence for the regulation of the expression of the recombinant nucleic acid.

5. The genetically modified cell according to claim 4, wherein the regulatory element for the regulation of the expression of the recombinant nucleic acid comprises a promoter nucleic sequence.

6. A method for the production of one or more HMOs, the method comprising the steps of:
  (i) providing the genetically modified cell of claim 1
  (ii) culturing the cell according to (i) in a suitable cell culture medium to express said recombinant nucleic acid, or said functional homologue thereof, whereby one or more HMOs are produced by the cultured genetically modified cell;
  (iii) harvesting the one or more HMOs produced in step (ii).

7. The method according to claim 6, wherein the one or more HMOs are selected from the group consisting of 2'-FL, 3-FL, DLF, LNT, LNT-II, LNnT, pLNnH and pLNH-II; or a mixture thereof.

8. The method according to claim 6, wherein the one or more HMOs are selected from the group consisting of 2'-FL and 3-FL; or a mixture thereof.

9. The genetically modified cell according to claim 5, wherein the regulatory element is a lac promoter or a glp promoter.

10. A method for the production of one or more human milk oligosaccharides, the method comprising the steps of:
  (i) providing the genetically modified cell of claim 9;
  (ii) culturing the cell according to (i) in a suitable cell culture medium to express said recombinant nucleic acid, whereby one or more HMOs are produced by the cultured genetically modified cell;
  (iv) harvesting the one or more HMOs produced in step (ii).

11. The method according to claim 10, wherein the genetically modified cell is *Escherichia coli*.

12. The method according to claim 10, wherein the one or more HMOs are selected from the group consisting of 2'-FL, 3-FL, DLF, LNT, LNT-II, LNnT, pLNnH and pLNH-II; or a mixture thereof.

13. The method according to claim 10, wherein the one or more HMOs are selected from the group consisting of 2'-FL and 3-FL; or a mixture thereof.

14. The method according to claim 10, wherein the one or more HMOs comprises 2'-FL.

15. The method according to claim 10, wherein the one or more HMOs comprises 3-FL.

* * * * *

SEQUENCE LISTING

<160> NUMBER OF SEQ ID NOS: 14

<210> SEQ ID NO 1
<211> LENGTH: 398
<212> TYPE: PRT
<213> ORGANISM: Serratia marcescens
<220> FEATURE:
<223> OTHER INFORMATION: Marc WP_060448169.1øptimized translation

<400> SEQUENCE: 1

Met Gln Arg Leu Ser Arg Leu Ser Leu Arg Ile Asn Pro Ile Phe Ala

```
1               5                   10                  15
Ala Phe Leu Leu Ile Ala Phe Leu Ser Gly Ile Ala Gly Ala Leu Leu
                20                  25                  30

Thr Pro Thr Leu Ser Leu Phe Leu Thr Thr Glu Val Lys Val Arg Pro
                35                  40                  45

Leu Trp Val Gly Leu Phe Tyr Thr Ala Asn Ala Val Ala Gly Ile Val
    50                  55                  60

Val Ser Phe Leu Leu Ala Lys Arg Ser Asp Thr Arg Gly Asp Arg Arg
65                  70                  75                  80

Arg Leu Ile Leu Leu Cys Cys Leu Met Ala Val Gly Asn Cys Leu Leu
                85                  90                  95

Phe Ala Phe Asn Arg Asp Tyr Leu Thr Leu Ile Thr Ala Gly Val Leu
                100                 105                 110

Met Ser Ala Val Ala Asn Thr Ala Met Pro Gln Ile Phe Ala Leu Ala
                115                 120                 125

Arg Glu Tyr Ala Asp Ser Glu Ala Arg Glu Val Met Phe Ser Ser
                130                 135                 140

Val Met Arg Ala Gln Leu Ser Leu Ala Trp Val Ile Gly Pro Pro Leu
145                 150                 155                 160

Ser Phe Ala Leu Ala Leu Asn Tyr Gly Phe Thr Val Met Phe Leu Ile
                165                 170                 175

Ala Ala Val Thr Phe Ala Val Cys Val Leu Leu Val Gly Phe Met Leu
                180                 185                 190

Pro Ser Val Pro Arg Ala Ala Glu Asn Glu Gly Leu Gln Gly Gly Val
                195                 200                 205

Ser Ala Pro Ile Ala Pro Ala Ser Ala Trp Arg Asn Arg Asp Val Arg
210                 215                 220

Leu Leu Phe Ile Ala Ser Met Leu Met Trp Thr Cys Asn Thr Leu Tyr
225                 230                 235                 240

Ile Ile Asp Met Pro Leu Tyr Ile Thr Ala Asp Leu Gly Leu Pro Glu
                245                 250                 255

Gly Leu Ala Gly Val Leu Met Gly Thr Ala Ala Gly Leu Glu Ile Pro
                260                 265                 270

Ala Met Leu Leu Ala Gly Tyr Tyr Val Lys Arg Phe Gly Lys Arg Asn
                275                 280                 285

Met Met Leu Leu Ala Val Val Ala Gly Val Leu Phe Tyr Leu Gly Leu
                290                 295                 300

Thr Val Leu Glu Ser Lys Pro Ala Leu Ile Ala Leu Gln Leu Leu Asn
305                 310                 315                 320

Ala Val Phe Ile Gly Ile Val Ala Gly Ile Gly Met Leu Tyr Phe Gln
                325                 330                 335

Asp Leu Met Pro Gly Arg Pro Gly Ala Ala Thr Thr Leu Phe Thr Asn
                340                 345                 350

Ser Ile Ser Thr Gly Val Ile Leu Ala Gly Val Leu Gln Gly Ala Leu
                355                 360                 365

Val Glu Asn Leu Gly His Gly Ser Val Tyr Trp Met Ala Ala Leu Leu
                370                 375                 380

Ala Leu Ala Ala Leu Gly Met Ser Ala Lys Val Arg Glu Val
385                 390                 395

<210> SEQ ID NO 2
<211> LENGTH: 1197
<212> TYPE: DNA
<213> ORGANISM: Serratia marcescens
```

<220> FEATURE:
<223> OTHER INFORMATION: marc nucleotide sequence

<400> SEQUENCE: 2

```
atgcagcgtc tgagccgtct gagcctgcgt atcaacccga ttttcgcggc gtttctgctg        60
atcgcgttcc tgagcggtat tgcgggtgcg ctgctgaccc cgaccctgag cctgtttctg       120
accaccgagg tgaaggttcg tccgctgtgg gtgggtctgt tctacaccgc gaacgcggtt       180
gcgggcatcg tggttagctt tctgctggcg aaacgtagcg acacccgtgg tgaccgtcgt       240
cgtctgattc tgctgtgctg cctgatggcg gtgggcaact gcctgctgtt cgcgtttaac       300
cgtgactacc tgaccctgat caccgcgggt gtgctgatga gcgcggttgc gaacaccgcg       360
atgccgcaga ttttcgcgct ggcgcgtgaa tatgcggata gcgaggcgcg tgaagtggtt       420
atgtttagca gcgtgatgcg tgcgcaactg agcctggcgt gggttattgg tccgccgctg       480
agcttcgcgc tggcgctgaa ctatggcttc accgtgatgt tctgattgc ggcggttacc        540
ttcgcggtgt gcgttctgct ggttggtttt atgctgccga gcgttccgcg tgcggcggag       600
aacgaaggcc tgcagggtgg cgtgagcgcg ccgattgcgc cggcgagcgc gtggcgtaac       660
cgtgacgttc gtctgctgtt tattgcgagc atgctgatgt ggacctgcaa cacccctgtac      720
atcattgaca tgccgctgta tatcaccgcg gatctgggtc tgccggaggg tctggcgggc       780
gtgctgatgg gcaccgcggc gggcctggaa atcccggcga tgctgctggc gggttactat       840
gttaagcgtt tcggcaaacg taacatgatg ctgctggcgg tggttgcggg tgtgctgttt       900
tacctgggcc tgaccgttct ggagagcaaa ccggcgctga ttgcgctgca gctgctgaac       960
gcggtgttca tcggtattgt tgcgggtatt ggcatgctgt attttcagga cctgatgccg      1020
ggtcgtccgg gtgcggcgac caccctgttc accaacagca tcagcaccgg cgtgattctg      1080
gcgggtgttc tgcaaggcgc gctggttgag aacctgggtc acggcagcgt ttactggatg      1140
gcggcgctgc tggcgctggc ggcgctgggt atgagcgcga agtgcgtga agtttaa         1197
```

<210> SEQ ID NO 3
<211> LENGTH: 300
<212> TYPE: DNA
<213> ORGANISM: Artificial Sequence
<220> FEATURE:
<223> OTHER INFORMATION: PglpF expression element

<400> SEQUENCE: 3

```
gcggcacgcc ttgcagatta cggtttgcca cacttttcat ccttctcctg gtgacataat        60
ccacatcaat cgaaaatgtt aataaatttg ttgcgcgaat gatctaacaa acatgcatca       120
tgtacaatca gatggaataa atggcgcgat aacgctcatt ttatgacgag gcacacacat       180
tttaagttcg atatttctcg tttttgctcg ttaacgataa gttacagca tgcctacaag        240
catcgtggag gtccgtgact ttcacgcata caacaaacat taaccaagga ggaaacagct       300
```

<210> SEQ ID NO 4
<211> LENGTH: 34
<212> TYPE: DNA
<213> ORGANISM: Artificial Sequence
<220> FEATURE:
<223> OTHER INFORMATION: Primer O40 backbone.for
<220> FEATURE:
<221> NAME/KEY: misc_RNA
<222> LOCATION: 9

<400> SEQUENCE: 4

```
attaacccuc caggcatcaa ataaaacgaa aggc                                    34
```

<210> SEQ ID NO 5
<211> LENGTH: 32
<212> TYPE: DNA
<213> ORGANISM: Artificial Sequence
<220> FEATURE:
<223> OTHER INFORMATION: Primer O79 Backbone.rev
<220> FEATURE:
<221> NAME/KEY: misc_RNA
<222> LOCATION: 10

<400> SEQUENCE: 5
atttgcgcau caccaatcaa attcacgcgg cc                                     32

<210> SEQ ID NO 6
<211> LENGTH: 32
<212> TYPE: DNA
<213> ORGANISM: Artificial Sequence
<220> FEATURE:
<223> OTHER INFORMATION: Primer O261, PglpF.for
<220> FEATURE:
<221> NAME/KEY: misc_RNA
<222> LOCATION: 10

<400> SEQUENCE: 6
atgcgcaaau gcggcacgcc ttgcagatta cg                                     32

<210> SEQ ID NO 7
<211> LENGTH: 36
<212> TYPE: DNA
<213> ORGANISM: Artificial Sequence
<220> FEATURE:
<223> OTHER INFORMATION: Primer O262, PglpF.rev
<220> FEATURE:
<221> NAME/KEY: misc_RNA
<222> LOCATION: 8

<400> SEQUENCE: 7
agctgttucc tccttggtta atgtttgttg tatgcg                                 36

<210> SEQ ID NO 8
<211> LENGTH: 31
<212> TYPE: DNA
<213> ORGANISM: Artificial Sequence
<220> FEATURE:
<223> OTHER INFORMATION: primer O737, marc.for
<220> FEATURE:
<221> NAME/KEY: misc_RNA
<222> LOCATION: 8

<400> SEQUENCE: 8
aaacagcuat gcagcgtctg agccgtctga g                                      31

<210> SEQ ID NO 9
<211> LENGTH: 32
<212> TYPE: DNA
<213> ORGANISM: Artificial Sequence
<220> FEATURE:
<223> OTHER INFORMATION: Primer O738, marc.rev
<220> FEATURE:
<221> NAME/KEY: misc_RNA
<222> LOCATION: 9

<400> SEQUENCE: 9
agggttaaut taaacttcac gcactttcgc gc                                     32

<210> SEQ ID NO 10
<211> LENGTH: 24

```
<212> TYPE: DNA
<213> ORGANISM: Artificial Sequence
<220> FEATURE:
<223> OTHER INFORMATION: Primer O48, galK.for

<400> SEQUENCE: 10
cccagcgaga cctgaccgca gaac                                              24

<210> SEQ ID NO 11
<211> LENGTH: 24
<212> TYPE: DNA
<213> ORGANISM: Artificial Sequence
<220> FEATURE:
<223> OTHER INFORMATION: Primer O49, glaK.rev

<400> SEQUENCE: 11
ccccagtcca tcagcgtgac tacc                                              24

<210> SEQ ID NO 12
<211> LENGTH: 203
<212> TYPE: DNA
<213> ORGANISM: Artificial Sequence
<220> FEATURE:
<223> OTHER INFORMATION: Promoter sequence PmglB_70UTR

<400> SEQUENCE: 12
tgcgtcgcca ttctgtcgca acacgccaga atgcggcggc gatcactaac tcaacaaatc       60
aggcgatgta accgctttca atctgtgagt gatttcacag tatcttaaca atgtgatagc      120
tatgattgca ccgtgcctac aagcatcgtg gaggtccgtg actttcacgc atacaacaaa      180
cattaaccaa ggaggaaaca gct                                              203

<210> SEQ ID NO 13
<211> LENGTH: 203
<212> TYPE: DNA
<213> ORGANISM: Artificial Sequence
<220> FEATURE:
<223> OTHER INFORMATION: Promoter sequence PmglB_70UTR_SD4

<400> SEQUENCE: 13
tgcgtcgcca ttctgtcgca acacgccaga atgcggcggc gatcactaac tcaacaaatc       60
aggcgatgta accgctttca atctgtgagt gatttcacag tatcttaaca atgtgatagc      120
tatgattgca ccgtgcctac aagcatcgtg gaggtccgtg actttcacgc atacaacaaa      180
cattaaccaa ctaggaaaca gct                                              203

<210> SEQ ID NO 14
<211> LENGTH: 291
<212> TYPE: DNA
<213> ORGANISM: Artificial Sequence
<220> FEATURE:
<223> OTHER INFORMATION: Promoter sequence PgatY_70UTR

<400> SEQUENCE: 14
cggcaaccta tgcctgatgc gacgctgaag cgtcttatca tgcctacata gcactgccac       60
gtatgtttac accgcatccg gcataaaaac acgcgcactt tgctacggct tccctatcgg      120
gaggccgttt ttttgccttt cactcctcga ataattttca tattgtcgtt tttgtgatcg      180
ttatctcgat atttaaaaac aaataatttc attatatttt gtgcctacaa gcatcgtgga      240
ggtccgtgac tttcacgcat acaacaaaca ttaaccaagg aggaaacagc t               291
```